US008580315B2

(12) United States Patent
DeVore et al.

(10) Patent No.: US 8,580,315 B2
(45) Date of Patent: *Nov. 12, 2013

(54) ANTI-INFLAMMATORY ACTIVITY OF EGGSHELL MEMBRANE AND PROCESSED EGGSHELL MEMBRANE PREPARATIONS

(75) Inventors: Dale Paul DeVore, Chelmsford, MA (US); Frank Daniel Long, Neosho, MO (US)

(73) Assignee: ESM Technologies, LLC, Carthage, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/683,268

(22) Filed: Mar. 7, 2007

(65) Prior Publication Data

US 2007/0178170 A1  Aug. 2, 2007

Related U.S. Application Data

(63) Continuation-in-part of application No. 10/797,747, filed on Mar. 10, 2004, now abandoned.

(60) Provisional application No. 60/743,412, filed on Mar. 7, 2006.

(51) Int. Cl.
*A61K 35/54* (2006.01)

(52) U.S. Cl.
USPC .......................................... 424/581; 514/886

(58) Field of Classification Search
USPC .......................................... 424/581; 514/886
See application file for complete search history.

(56) References Cited

U.S. PATENT DOCUMENTS

| | | | |
|---|---|---|---|
| 3,194,732 A | 7/1965 | Neuhauser | |
| 3,558,771 A | 1/1971 | Balassa | |
| 4,141,973 A | 2/1979 | Balazs | |
| 4,517,295 A | 5/1985 | Bracke et al. | |
| 4,713,448 A | 12/1987 | Balazs et al. | |
| 4,716,224 A | 12/1987 | Sakurai et al. | |
| 4,784,990 A | 11/1988 | Nimrod et al. | |
| 4,879,375 A | 11/1989 | Cullis-Hill | |
| 4,992,264 A | 2/1991 | Diot et al. | |
| 5,079,236 A | 1/1992 | Drizen et al. | |
| 5,099,013 A | 3/1992 | Balazs et al. | |
| 5,141,964 A | 8/1992 | Noel | |
| 5,166,331 A | 11/1992 | della Valle et al. | |
| 5,316,926 A | 5/1994 | Brown et al. | |
| 5,411,874 A | 5/1995 | Ellwood et al. | |
| 5,415,875 A | 5/1995 | Kakoki et al. | |
| 5,460,832 A | 10/1995 | Yamaguchi et al. | |
| 5,538,740 A | 7/1996 | Abad | |
| 5,559,104 A | 9/1996 | Romeo et al. | |
| 5,646,129 A | 7/1997 | Callegaro et al. | |
| 5,714,582 A | 2/1998 | Wolfinbarger | |
| 5,772,999 A | 6/1998 | Greenblatt et al. | |
| 5,783,691 A | 7/1998 | Malson et al. | |
| 5,869,063 A | 2/1999 | Lezdey et al. | |
| 5,925,626 A | 7/1999 | della Valle et al. | |
| 5,928,659 A | 7/1999 | Moy | |
| 6,025,334 A | 2/2000 | Dupont et al. | |
| 6,028,118 A | 2/2000 | Dupont et al. | |
| 6,030,958 A | 2/2000 | Burns et al. | |
| 6,090,596 A | 7/2000 | Stahl | |
| 6,176,376 B1 | 1/2001 | MacNeil | |
| 6,194,392 B1 | 2/2001 | Falk et al. | |
| 6,217,913 B1 | 4/2001 | Mohammadi | |
| 6,218,373 B1 | 4/2001 | Falk et al. | |
| 6,255,295 B1 | 7/2001 | Henderson et al. | |
| 6,337,389 B1 | 1/2002 | Wolfinbarger, Jr. | |
| 6,399,083 B1 | 6/2002 | Pillai et al. | |
| 6,498,204 B1 | 12/2002 | Ubara | |
| 6,649,203 B1 | 11/2003 | Thoroski | |
| 6,706,267 B1 | 3/2004 | Adalsteinsson et al. | |
| 6,899,294 B2 | 5/2005 | MacNeil | |
| 6,946,551 B2 * | 9/2005 | Long et al. | 536/55.3 |
| 7,007,806 B2 | 3/2006 | MacNeil | |
| 7,017,277 B1 | 3/2006 | Adams et al. | |
| 2002/0037312 A1 | 3/2002 | Brown et al. | |
| 2003/0175332 A1 | 9/2003 | Brown et al. | |
| 2004/0156857 A1 | 8/2004 | Adalsteinsson et al. | |
| 2004/0180025 A1 | 9/2004 | Long et al. | |
| 2006/0159816 A1 | 7/2006 | Vlad | |

FOREIGN PATENT DOCUMENTS

| | | |
|---|---|---|
| JP | 1043502 | 2/1989 |
| JP | 01-275512 | 11/1989 |
| JP | 03-045264 | 2/1991 |
| JP | 3-255014 | 11/1991 |
| JP | 4-1486649 | 5/1992 |
| JP | 04148649 A * | 5/1992 |

(Continued)

OTHER PUBLICATIONS

Kataoka, S., "Composition for oral cavity and ophthalmology", Apr. 3, 2001, JP 2001-089383, machine translation.*
Yamashita, M. et al., "Production of Water-Soluble Shell Membrane", May 21, 1992, JP04-148649, translation (PTO 09-4086).*
Blakiston's Gould Medical Dictionary, 1979, McGraw-Hill Book Company, (4th ed.), pp. 93, 676, 1022.*
Yamashita, M. et al. "Production of water-soluble shell membrane", May 21, 1992, JP 04148649, English translation (PTO09-4086).*
Numagami, K. et al. "Moisturizing effect on the stratum corneum of skin lotion containing egg shell and membrane powder evaluated by high frequency conductance in healthy human volunteers", 1999, Skin Research, No. 41, No. 3, pp. 387-390, English abstract.*

(Continued)

*Primary Examiner* — Gina C Justice
(74) *Attorney, Agent, or Firm* — Hoffmann & Baron, LLP

(57) ABSTRACT

The present invention relates to anti-inflammatory activity of eggshell membrane, processed eggshell membrane preparations and eggshell membrane isolates. The invention is directed to eggshell membrane compositions exhibiting anti-inflammatory activity as measured by effects on down-regulating pro-inflammatory plasma antigens in mammals that had orally ingested such compositions. This information supports the potential benefits from administration of naturally occurring material found in eggshell membrane, processed eggshell membrane, eggshell membrane isolates and combinations to reduce pain and inflammation associated with arthritis and other inflammatory conditions.

15 Claims, No Drawings

(56) References Cited

FOREIGN PATENT DOCUMENTS

| JP | 05-097897 | | 4/1993 |
|---|---|---|---|
| JP | 05097897 | | 4/1993 |
| JP | 5-178735 | | 7/1993 |
| JP | 08173838 | | 7/1996 |
| JP | 11-193279 | | 7/1999 |
| JP | 11-215968 | | 8/1999 |
| JP | 2000-344798 | | 12/2000 |
| JP | 2001-089383 | * | 4/2001 |
| JP | 2001-89383 | | 4/2001 |
| JP | 2002249440 | | 9/2002 |
| JP | 2003125731 A | * | 5/2003 |
| JP | 2003246741 A | * | 9/2003 |
| JP | 2005145889 | | 6/2005 |

OTHER PUBLICATIONS

Ri, R. et al., "Health Food", May 7, 2003, JP02003125731A, English abstract.*
Kanemitsu, S. et al. "Oral skin improving agent for use in foodstuffs, comprises eggshell membrane or its hydrolysed substance as essential ingredient", Sep. 2, 2003, Derwent-Acc-No. 2003-820953, machine translation.*
Dorland's Illustrated Medical Dictionary, 30th Edition, 2003, pp. 1065 and 1848.
Yi F. et al., "Soluble eggshell membrane protein:preparation, characterization and biocompatibility", NCBI PubMed, Biomaterials, Aug. 2004;25(19):4591-9, www.ncbi.nlm.nih.gov.
Ino T. et al., "Improved physical and biochemical features of a collagen membrane by conjugating with soluble egg shell membrane protein", NCBI PubMed, Biosci Biotechnol Biochem, Apr. 2006; 70(4):865-73.
Harris, Blount, Leach Jr., "Localization of lysyl oxidase in hen oviduct:implications in egg shell membrane formation and composition" Science, Apr. 4, 1980;208(4439):55-6.
Arias, Fernandez, Dennis, Caplan, "Collagens of the chicken eggshell membranes", Connect Tissue Res. 1991;26(1-2):37-45.
Arias, Fernandez, Dennis, Caplan, "The fabrication and collagenous substructure of the eggshell membrane in the isthmus of the hen oviduct", Matrix, Nov. 1991;11(5):313-2.
Gautron, Hincke, Panheleux, Garcia-Ruiz, Boldicke, Nys, "Ovotransferrin in a matrix protein of the hen eggshell membranes and basal calcified layer", Connect Tissue Res. 2001;42(4):255-67.
Starcher, King, "The presence of desmosine and isodesmosine in eggshell membrane protein", Connect Tissue Res. 1980;8(1):53-5.
Adagawa, Wako, Suyama, "Lysyl oxidase coupled with catalase in egg shell membrane", Biochim Biophys Acta, Sep. 14, 1999;1434(1):151-60.
Wu et al., "Crystallization Studies on Avian Eggshell Membranes: Implications for the Molecular Factors Controlling Eggshell Formation", Matrix Biology vol. 14/1994, pp. 507-513.
Powrie William D., Nakai, S., "The Chemistry of Eggs and Egg Products" Egg Science and Technology, Third Edition, 1990 Food Products Press subsidiary of the Haworth Press, Inc., Binghamton, NY.
Baker J. R. and Balch D. A., "A Study of the Organic Material of Hen's-Egg Shell", Biochem. J. (1962)vol. 82, 352-61.
Wong et al., "Collagen in the Egg Shell Membranes of the Hen", Evelopmental Biology 104, 28-36 (1984).
Arias et al., "Role of Type X Collagen on Experimental Mineralization of Eggshell Membranes", Connective Tissue Research, vol. 36(1), pp. 21-33, 1997 Overseas Publishers Association.
Picard J. et al., "Sulfated glycoproteins from egg shell membranes and hen oviduc. Isolation and characterization of sulfated glycopeptides" "Glycoproteines Sulfates Des Membranes De L'oeuf De Poule et de L'Oviducte. Isolement et Caracterisation de Glycopeptides Sulfates", Biochimica et Biophysica Acta, 320(1973)427-441 Elsevier Scientific Publishing Company, Amsterdam.
Hincke M. T. et al., Purification and Immunochemistry of a Soluble Matrix Protein of the Chicken Eggshell (Ovocleidin 17), Calcified Tissue International (1995) 56:578-583 Springer-Verlag New York, Inc.
Dray, "Inflammatory Mediators of Pain", British Journal of Anaesthesia 1995; 75:125-131.
Haringman J. J. et al., "Chemokines in joint disease: the key to inflammation?", Ann Rheum Dis 2004;63:1186-1194.
Dinarello, Charles A., "Impact of Basic Research on Tomorrow's Medicine—Proinflammatory Cytokines", Chest/118/2/Aug. 2000.
Martel-Pelletier, J. et al. "Cytokines and their role in the Pathophysiology of Osteoarthritis", Frontiers in Bioscience 4, d694-703, Oct. 15, 1999.
Stanczyk et al., "Rantes and Chemotactic Activity in Synovial Fluids from Patients with Rheumatoid Arthritis and Osteoarthritis", Mediators of Inflammation, Jun. 2005 (2005) 343-348, 2005 Hindawi Publishing Corporation.
Bless et al., "Role of CC Chemokines (Macrophage Inflammatory Protein-1B, Monocyte Chemoattractant Protein-1, Rantes) in Acute Lung Injury in Rats", 2000 The American Association of Immunologists.
Long et al., "Herbal Medicines for the treatment of osteoarthritis: a systematic review", Rheumatology 2001;40:779-793, 2001 British Society for Rheumatology.
Nakano, T. et al., "Chemical composition of chicken eggshell and shell membranes", Poult Sci. 2003, 82 (3):510-4.
Dopoirieux L, et al, "Comparative study of three different membranes for guided bone regeneration of rat cranial defects", Int J Oral Maxillofac Surg. 2001, 30(1):58-62 [Abstract].
Hincke MT, et al., "Identification and Localization of lysozyme as a component of eggshell membranes and eggshell matrix", Matrix Biol 2000, 19(5):443-53 [Abstract].
Dupoirieux L., et al.,"Comparision of pericranium and eggshell as space fillers used in combination with guided bone regeneration: an experimental study", J Oral Maxillofac Surg 2000, 58(1): 40-6 [Abstract].
Osuoji Ci, "Acid glycosaminoglycan of eggshell membranes", Biochim Biophys Acta 1971, 244(2):481-3.
Gautron, J., et al., Ovotransferrin is a matrix protein of the hen eggshell membranes and basal calcified layer, Connect Tissue Res 2001, 42(4):255-67 [Abstract].
Suyama K., et al., "A new biomaterial, hen egg shell membrane, to eliminate heavy metal ion from their dilute waste solution", Appl Biochem Biotechnol 1994, 45-46:871-9 [Abstract].
Robel, U.S. Dept. of Agriculture, Avian Physiology Laboratory, Beltsville, Maryland 20705, "Levels of calcium and soluble collagen in turkey egg shell membranes", Comp Biochem Physiol A 1988, 90(3):421-4 [A bstract].
Leach, RM Jr., et al., "Egg shell membrane protein: a nonelastin desmosine/isodesmosine-containing protein", Arch Biochem Biophys 1981, 207(2):353-9 [Astract].
Crombie G "Lysine-derived cross-links in the egg shell membrane", Biochim Biophys Acta 1981, 640(1):365-7 [Abstract].
Harris Ed, et al., "Localization of lysyl oxidase in hen oviduct: implications in egg shell membrane formation and composition", Science 1980, 208(4439):55-6 [Abstract].
Stevenson IL, "The removal of egg shell membranes by enzyme treatment to facilitate the study of shell microstructure", Poult Sci 1980, 59(8):1959-60 [Abstract].
U.B.G. Laurent, "Hyaluronate in Human Aqueous Humor", Arch Ophtalmol., vol. 101 (1983) pp. 129-130., vol. 101 (1983) pp. 129-130.
Wu Tzong-Ming, et al, "Crystallization Studies on Avian Eggshell Membranes: Implications for the Molecular Factors Controlling Eggshell Formation", Matrix Biology 1995, 14:507-513.
Gautron, Bain M., et al., "Soluble matrix of hen's eggshell extracts changes in vitro the rate of calcium carbonate precipitation and crystal morphology", British Poultry Science 1996 37, 853-866.
Tomihata, Kenji, et al, "Crosslinking of hyaluronic acid with water-soluble carbodiimide", J Biomed Mater Res, 1997, 37, 243-251.
Carrino, David, et al., "The Avian Eggshell Extracellular Matrix as a Model for Biomineralization", Connective Tissue Research, 1996, 35(1-4), 325-329.

(56) References Cited

OTHER PUBLICATIONS

Powrie et al., "The Chemistry of Eggs and Egg Products,", Egg Science and Technology, Eds. W.J. Stadelman and O.J. Cotterill, Food Products Press, a subsidiary of The Haworth Press, Bingham, NY, 1990.

Britton, W.M., et al., "Amino Acid Analysis of Shell Membranes of Eggs from Young and Old Hens Varying in Shell Quality", Poultry Science, 56:865-871, 1977.

Cifonelli, J.A., "The Colormetric Estimation of Uronic Acid", Methodology of Connective Tissue Research, ED:DA Hall, Joynson-Bruvvers Ltd., Oxford 1976, Chapter 26, pp. 253-256.

Armstrong, DC, et. al., "Improved Molecular Weight Analysis of *Streptococcal hyaluronic* Acid by Size Exclusion Chromatography" in Biotechnology Techniques, 1995.

Fernandez, M.S., Araya, M., and Arias, JL, "Eggshells are Shaped by a Precise Spatio-Temporal Arrangement of Sequentially Deposited Macromolecules", Matrix. Biol., 16:13-20, 1997.

Takahashi, K., Shirai, K., Kitamura, M., Hattori, M., "Soluble Egg Shell Membrane Protein as a Regulating Material for Collagen Matrix Reconstruction", Biosci. Biotechnology & Biochemistry, 60:1299-1302, 1996.

T.C. Laurent, "Structure of Hyaluronic Acid", Chem. and Mol. Biol. of Intracellular Matrix, vol. 2, 1970, pp. 703-732.

O.H. Lowry et al., "Protein Measurement with the Folin Phenol Reagent", The Journal of Biological Chemistry, vol. 193 (1951) pp. 265-275.

W.D. Comper et al., "Physiological Function of Connective Tissue Polysaccharides", Physiological Reviews, vol. 58, No. 1 (1978) pp. 255-315.

K. Meyer, "Chemical Structure of Hyaluronic Acid", Fed. Proceed, vol. 17 (1958) pp. 1075-1077.

E.A. Balazs et al., "Hyaluronic Acid and Replacement of Vitreous and Aqueous Humor", Mod. Probl. Ophthal., vol. 10 (1972) pp. 3-21.

\* cited by examiner

ANTI-INFLAMMATORY ACTIVITY OF EGGSHELL MEMBRANE AND PROCESSED EGGSHELL MEMBRANE PREPARATIONS

CROSS-REFERENCE TO RELATED APPLICATIONS

This application is a continuation-in-part of U.S. patent application Ser. No. 10/79747 filed on Mar. 10, 2004 and claims priority of an earlier filed U.S. Provisional Patent Application No. 60/743,412, filed on Mar. 7, 2006.

BACKGROUND OF THE INVENTION

The present invention relates to anti-inflammatory activity of eggshell membrane, processed eggshell membrane preparations and eggshell membrane isolates and combinations thereof.

Eggshell membrane is composed of two individual membranes between egg albumin and eggshell. The membranes are primarily comprised of protein fibers. The fibers appear to be a network or scaffold predominantly containing Type I collagen fibers that are encapsulated in a continuous mantle of proteoglycans and other macromolecules. (see T-M, et. al., Matrix Biology, 14:507-513, 1994). The thickness of the two membranes ranges from 73-114 μm in eggs from White Leghorn and New England pullets. (see "Egg Science and Technology" Eds. W. J. Stadelman and O. J. Cotterill, Food Products Press, a subsidiary of The Haworth Press, Bingham, N.Y., 1990) The outer membrane has a thickness ranging from 53.2 μm to 65.5 μm in White Leghorn eggs while the inner membrane ranges form 19.5 μm to 24.3 μm.

Britton and Hale reported that the proteins of shell membranes exhibited a high content of arginine, glutamic acid, methionine, histidine, cystine, and proline. (see Britton, W. M. and hale, K. K., Poultry Science, 56:865-871, 1977) Baker and Balch and Harris, et. al. found that eggshell membranes also contained hydroxyproline, hydroxylysine, and desmosine. (see Baker, J. R. and Balch, D. A., Biochem. J., 82: 352-361, 1962; see also Harris, E. D., Blount, J. E. and Leach, R. M., Science, 200: 55-56, 1980) Subsequent studies by Wong et. al. demonstrated the presence of Type I and Type V collagen in eggshell membrane. (see Wong, M, et. al., Dev. Biology, 104:28-36, 1984) Arias, et. al. subsequently identified the presence of Type X in eggshell membrane and postulated that Type X collagen functions to inhibit mineralization and establishes a zone protected from mineral deposition. (see Arias, J. L., et. al., Connective Tissue Research, 26: 37-45, 1991; Aria, J. L., et. al., Matrix, 11: 313-320, 1991; see also Arias, J. L., et. al., Connective Tissue Research, 36: 21-33, 1997)

Eggshell membrane also has been shown to contain acid glycosaminoglycans including dermatan sulfate and chondroitin-4-sulfate. Picard, et. al., isolated and characterized sulfated glycoproteins from eggshell membrane. (see Picard, J., Paul-Gardais, A., and Vedel, M, Biochimica et Biophysica Acta, 320: 427-441) Glycoproteins included hexosamines, hexoses, and fucose. More recently, significant amounts of hyaluronic acid have been detected in eggshell membrane (U.S. Pat. No. 6,946,551.). Other components identified in eggshell membrane include ovotransferrin, desmosine and isodesmosine, lysyl oxidase, and lysozyme. (see Gautron, J., et. al., Connective Tissue Research, 42:255-267, 2001; Starcher, B. C. and King, G. S., Connective Tissue Research, 8:53-55, 1980; and Akagawa, M, et. al., Biochim. Biophys. Acta, 14:151-160, 1999; Hincke, M. T., et. al. Matrix Biology, 19:443453, 2000)

Eggshell membranes are examples of collagenous structures that support development. The most evident function of the membrane is to act as a supporting structure for the egg prior to deposition of a calcified shell and to provide an organic matrix for the deposition of calcium in eggshell formation. The membrane might also be inductive to the developing embryo via secretion of growth factors. The proposed inductive characteristics of eggshell membrane along with its high protein content and significant quantities of glucosamine, chondroitin sulfate, and hyaluronic acid support its potential utility in therapeutics and nutraceuticals.

Compositions, isolates, and proteins from other natural sources have been previously described for therapeutic, cosmetic, and nutraceutical applications. For example, processed antler powder has been suggested for use in nutraceutical compositions containing such powder. The powder is placed in nutraceutical capsules, formed into tablets or used as an ingredient in nutritional bars or beverages. Methods of preparing lipid fractions from sea cucumbers that can be used as nutraceutical supplements to ameliorate immune responses have also been suggested. The isolates are identified as being useful in the treatment of allergic diseases, inflammatory diseases, and hyperproliferative skin diseases. The preparations may be administered orally or formulated into a topical lotion. Others have disclosed the preparation of milk protein hydrolysates and applications for use in cosmetic formulations. The hydrolysates are described as having skin hydrating properties and wound healing characteristics.

Additional examples of materials derived from natural sources, that have been suggested as therapeutic ingredients, include a protein hydrolysate prepared from poultry feet and processed into a powder or gel for use treating burns or for regrowing muscle, skin, and nerve tissues; a method for treating diseased or injured abraded, lacerated, or ulcerated tissue by applying a composition containing sucrose, gelatin, and water; a method and agent for treating inflammatory disorders of the gastrointestinal tract by administering D-glucosamine hydrochloride in solid or liquid form; and compositions containing amino sugars, such as glucosamine, and a glycosaminoglycan, such as chondroitin, to protect, treat and repair connective tissue.

Other oral and topical compositions derived from natural sources for protection, treatment, and repair of connective and skin tissues have been disclosed. For example, an oral and injectable composition comprised of glucosamine, chondroitin sulfate, hydrolyzed or native collagen, sodium hyaluronate, chelated manganese ascorbate, and L-malic acid. The composition acts as a chondroprotective agent, enhances chondrocyte synthesis, healing wounds, and maintaining healthy tissue. Compositions containing glucosamine, chondroitin sulfate, and optionally manganese ascorbate have also been suggested. The topical application or injection of 40-55 wt. % chondroitin sulfate to protect joint cells, reduce aseptic inflammation, and preserve human and animal cells in vitro has also been described. Topical preparations for improving wound healing have also been suggested which include a suspension of collagen and a glycosaminoglycan.

Although certain components (that have now been identified to be present in significant quantities in eggshell membrane, i.e., collagen, glucosamine, chondroitin sulfate, and hyaluronic acid), have been disclosed as being useful in therapeutic and nutraceutical applications, the potential anti-inflammatory activity of processed eggshell membrane and/or eggshell membrane isolates in accordance with the present invention have not been previously described.

Inflammation, as defined in Dorland's Medical Dictionary, is "a localized protective response, elicited by injury or destruction of tissues, which serves to destroy, dilute or wall off both the injurious agent and the injured tissue." It is characterized by fenestration of the microvasculature, leakage of the elements of blood into the interstitial spaces, and migration of leukocytes into the inflamed tissue. On a macroscopic level, this is usually accompanied by the familiar clinical signs of erythema, edema, hyperalgesia (tenderness), and pain.

The inflammatory response is any response characterized by inflammation as defined above. It is well known, to those skilled in the medical arts, that the inflammatory response causes much of the physical discomfort (i.e., pain and loss of function) that has come to be associated with different diseases and injuries.

A number of mediators of inflammation also act as mediators of pain. Dray and LaBars discuss several cytokines released from immune cells that are able to induce hyperalgesia. (see Dray, A. Inflammatory Mediators in Pain. Brit. J. Anaesthesia. 75:125-131; see also LeBars, D and Adam, F., Nociceptors and Mediators in Acute Inflammatory Pain. 2002. Ann. Fr. Anesth. Reanim. 4:315-335) These cytokines include IL-10, IL-6, IL-8 and TNFα. Hyperalgesia is mediated indirectly via several mechanisms including prostanoid release, increasing nerve growth factor (NGF) or braydkinin receptors or affecting sympathetic fibres.

Cytokines are regulators of host responses to infection, immune responses, inflammation and trauma. Some cytokines make disease worse (pro-inflammatory) and some reduce inflammation and promote wound healing (anti-inflammatory).

Pro-inflammatory cytokines include IL-1α, IL-1β, IL-11, IL-12, IL-17, IL-18, TNFα, monocyte chemoattractant protein (MCP-1, MCP-3, MCP-5), RANTES (RANTES is an acronym for Regulated on Activation, Normal T Expressed and Secreted; It is also known as CCL5), and Macrophage Inflammatory Protein (MIP-1β, MIP-2, MIP-3β). (see Haringham, J J, Ludikhuize, J. and Tak, P P. Chemokines in Joint Disease: the Key to Inflammation? 2005. Ann. Rheum. Dis. 63:1186-1194; Dinarello, C A. Proinflammatory Cytokines. 2000. Chest 118:503-508; Martel-Pelletier, J, Alaaeddine, N, and Pelletier, J-P, Cytokines and Their Role in the Pathophysiology of Osteoarthritis, 1999. Frontiers in Bioscience, 4: 694-703; Stancyk, J., Marekl, L K, Grzegorczyk, J, Szkudlinksa, B, Jarzebska, M, Marciniak, M, and Snyder, M. RANTES and Chemotactic Activity in Synovial Fluids from Patients with Rheumatoid Arthritis and Osteoarthritis. Mediators of Inflammation, 6:343-348; and Bless, N M, Huber-Lang, M, Guo, R-F, Warner, R L, Schmal, H, Czermak, B H J, Shanley, T P, Crouch, L D, Lentsch, A B, Sarma, V, Mulligan, M S, Friedl, H P, and Ward, P A, Role of CC Chemokines (Macrophage Inflammatory Protein-1β, Monocyte Chemoattractant Protein-a, RANTES) in Acute Lung Injury in Rats. J. Immunology, Vol. 164:2650-2659)

Anti-inflammatory cytokines include IL-6, IL-10, IL-12, and IL-13.

Treatments for Inflammation include a variety of anti-inflammatory agents (COX enzyme inhibitors), slow acting, disease-modifying agents, including nutraceuticals such as glucosamine and chondroitin sulfate (Millis) and a number of herbal medicines, including Articulin-F, Avocado, Capsaicin, Devils' Claw, Ginger, Phytodolor, Reumalex, Stinging nettle, and Willow bark (reviewed by Long, et. al.) (see Millis, DL. New Treatments for Osteoarthritis. www.vet.utk.edu; see also Long, L., Soeken, K, and Ernst, E. 2001. Herbal medicines for the treatment of osteoarthritis: a systematic review, Rheumatology 40:779-793.)

U.S. Pat. No. 6,706,267 to Adalsteinsson, et. al., discloses a composition and method for the treatment and prevention of inflammation and inflammatory related disorders. The composition is glucosamine in combination with an egg product. It is generally preferred that the egg product is obtained from an avian which has been hyperimmunized with an immungenic mixture and/or which contains an anti-inflammatory composition. The whole egg comprises an anti-inflammatory composition. The invention is also directed to a method for reducing inflammation in a subject, the method comprising administering to the subject an effective amount of glucosamine and an egg product. While the patent defines "egg product" as any whole egg (table, hyperimmunized or otherwise) or any product or fraction derived therefrom, the invention does not disclose the potential anti-inflammatory activity of the eggshell membrane, hydrolysates or isolates of eggshell membrane and combinations thereof.

Thus, it has not been previously reported to use processed eggshell membrane and/or eggshell membrane isolates as nutraceuticals to protect, treat, and repair of connective tissues, or to reduce joint pain and inflammation related to osteoarthritis, rheumatoid arthritis or other joint disorders.

Further, it has not been previously reported that processed eggshell membrane and/or eggshell membrane isolates exhibit anti-inflammatory properties based on reduction of pro-inflammatory plasma cytokine levels in animals consuming processed eggshell membrane and/or eggshell membrane isolates.

Therefore, processed eggshell membrane and/or eggshell membrane isolates provide a natural composition for potential application in reducing inflammation and pain associated with arthritis and other diseases and disorders exhibiting inflammation and/or pain.

BRIEF SUMMARY OF THE INVENTION

The present invention describes the unexpected benefits of eggshell membrane, processed eggshell membrane and eggshell membrane isolates and hydroysates and combinations thereof in reducing the levels of pro-inflammatory plasma cytokines. Such compositions may be used for therapeutic and nutraceutical applications in reducing chronic pain and discomfort associated with inflammation.

The inventors have investigated the anti-inflammatory activity of eggshell membrane, which was cleanly separated from egg and eggshell and combined with eggshell membrane hydrolysate, by analyzing for plasma antigens in animals (rats). Effects of oral NEM administration on systemic inflammatory cytokines was evaluated using a novel, multi-analyte immunoassay profile of 60 acute phase reactants, cytokines, growth factors, and hormones using the Rules Based Medicine technology at Charles River Laboratories (Charles River Laboratories, Preclinical Services, 640 N. Elizabeth St., Spencerville, Ohio 45887).

Results clearly demonstrated that processed eggshell membrane and eggshell membrane hydrolysate reduced plasma pro-inflammatory cytokines, typically associated with inflammation and pain.

In one embodiment, the invention is directed to a nutraceutical composition containing a safe and effective amount of a therapeutically active component which includes naturally occurring therapeutically active material derived from eggshell membrane. The active material derived from eggshell membrane is preferably selected from the group consisting of eggshell membrane powder, an eggshell membrane hydrolysate, an eggshell membrane isolate and combinations thereof.

In one embodiment, the active material includes a combination of an eggshell membrane powder and an eggshell membrane hydrolysate or isolate, or a combination of different eggshell membrane hydrolysates or isolates.

In yet another embodiment, the invention is directed to a method for treating a mammal having a condition that will benefit from the administration of a natural material found in eggshell membrane, the method involving administering to the mammal a composition which includes a naturally occurring therapeutically active material derived from eggshell membrane.

In one embodiment the condition is a condition having an inflammatory component and the administering step includes orally or parentally administering the composition to the mammal, in an amount sufficient to treat the condition. The condition having an inflammatory component can be selected from the group consisting of osteoarthritis; rheumatoid arthritis; rheumatism; bursitis; degenerative spinal disc disease; a degenerative condition causing joint, tendon, ligament or soft tissue pain; and trauma to joints, tendons, ligaments or soft tissue.

BRIEF DESCRIPTION OF THE DRAWINGS

Not Applicable

DETAILED DESCRIPTION OF THE INVENTION

The present invention describes therapeutic and nutraceutical applications of eggshell membrane, processed eggshell membrane and eggshell membrane isolates.

The eggshell membrane, processed eggshell membrane and eggshell membrane hydrolysates and isolates are preferably free of any animal body components or trace thereof, e.g., animal tissue, blood or body fluid components, which are detrimental or undesirable for the contemplated use of the products or product combinations.

The invention is directed to compositions, and methods of using the compositions, which contain eggshell membrane, processed eggshell membrane, eggshell membrane isolates and/or extracts, and combinations thereof. The eggshell membrane material is obtained by methods that preferably include the step of separating the eggshell membrane from the egg yolk, egg white and eggshell prior to subsequent processing and isolation steps.

Typically, the source of eggshell membrane will be from cracked eggs, where the eggshell membrane is still attached to the eggshell. The eggshell membrane can be separated from the eggshell in any convenient manner. Preferably, the eggshell membrane is separated from the eggshell in the absence of any unwanted substance that would remain in the source material, e.g., the eggshell membrane. Unwanted substances will primarily include calcium carbonate from eggshell residuals. However, small amounts of this calcium source may be beneficial in certain applications, i.e., nutraceuticals.

Methods for separating eggshell membrane from the eggshell can include a purely mechanical manner as, for instance, by rolling and pulling the membranes away from the washed shells after removal of the yoke and albumen of fresh or uncooked eggs. Mechanical methods of separating eggshell membranes from cooked eggs are also contemplated.

A combination of mechanical and chemical means of separating the eggshell membrane from the eggshell can also be used, such as agitating coarsely chopped eggshells containing the adhering membranes in the presence of a dilute acid until the membrane separates from the shell and separating the released membranes from the shells. U.S. Pat. No. 3,194,732 to Neuhauser provides a more detailed discussion of methods for separating eggshell membrane from eggshells, which is incorporated herein by reference.

The method also preferably includes dehydrating the separated eggshell membrane to produce eggshell membrane flakes of various dimensions.

The method also preferably includes powdering the eggshell membrane flakes to produce an eggshell membrane powder with a particle size between 100-500 microns. Powdering is accomplished using standard milling or pulverizing procedures to treat eggshell membrane flakes containing about 10% moisture. Sizing is conducted using a series of screens.

In another method, powdered eggshell membrane is subjected to enzymatic hydrolysis using a yeast enzyme. The resulting slurry contains a soluble fraction containing predominantly hyaluronic acid and other aqueous soluble fractions and an insoluble fraction containing predominantly collagens and other insoluble fractions.

It is preferred that the eggshell membrane isolates, extracts and hydrolysates are prepared without substantially altering the natural ingredients found in the eggshell membrane. Preferably, the ingredients found naturally in the eggshell membrane which have properties useful for nutraceuticals and pharmaceuticals are not substantially altered as a result of the processes used to prepare the isolates, extracts or hydrolysates.

By the terminology "natural material," "naturally occurring material" or "naturally occurring active material" derived from eggshell membrane is intended material derived from eggshell membrane which contains a significant amount of at least one ingredient or component of the eggshell membrane that is substantially unaltered from the untreated or unprocessed eggshell membrane, in terms of its function as an ingredient useful for cosmetics, nutraceuticals or pharmaceuticals. By substantially unaltered is meant that the selected or desired ingredient(s) or component(s) substantially retain(s) its/their physical characteristics and is/are not significantly decomposed, digested or cleaved. However, other components or ingredients may be altered in certain isolates or hydrolysates. For example, hydrolysates prepared by enzyme treatment may result in naturally occurring proteins being at least partially digested. Preferably, the majority of the naturally occurring ingredients found in the eggshell membrane are substantially unaltered and, more preferably, substantially all of the naturally occurring ingredients are substantially unaltered. Although the physical characteristics of individual components of the eggshell membrane remain substantially unaltered, the overall composition or amounts of different components can be altered depending on the desired composition for a particular isolate, extract or hydrolysate.

Thus, in one embodiment, the invention is directed to compositions for use with mammals, including both humans and animals. The compositions include naturally occurring constituents derived from eggshell membrane that are useful to humans or animals.

By the terminology "use with mammals," is intended treatment of a mammal having any condition, which would benefit from the administration of eggshell membrane preparation or eggshell membrane isolates or combinations of any naturally occurring constituents from the eggshell membrane, as well as inclusion of the composition in any product intended for use by mammals. Uses of the composition can include use as an ingredient in nutraceuticals or pharmaceuticals. Preferred uses include an orally administered nutraceutical or a locally administered composition for treatment of joints afflicted with osteoarthritis. Other uses include use as a vehicle for other pharmacological substances, in wound healing, treatment of periodontal diseases and as an osteoinductive agent.

In one embodiment, the invention is directed to compositions which contain naturally occurring therapeutically active material derived from eggshell membrane. The compositions can include mechanically processed eggshell membrane, such as flakes or powder, or eggshell membrane isolates or extracts. The eggshell membrane isolates can be in liquid, semi-solid or solid form, e.g., partially dehydrated powdered form containing varying amounts of liquid or moisture.

In another embodiment, the invention is directed to a therapeutic composition which includes a naturally occurring material derived from eggshell membrane in combination with a therapeutically acceptable carrier or vehicle.

The term "therapeutic composition" is intended for the purposes of the present invention to mean any composition or agent administered to a mammal that confers a therapeutic effect to the mammal. The therapeutic composition can be administered topically, orally or parenterally to the mammal.

In another embodiment, the invention is directed to methods of treating a mammal having a condition which will benefit from the administration of naturally occurring eggshell membrane substances, including eggshell membrane preparations, eggshell membrane isolates and combinations thereof. Such conditions can include, for example, conditions involving connective tissue injuries or degeneration; conditions involving an inflammatory response, such as osteoarthritis, rheumatoid arthritis or other joint disorders; wounds; and dry or wrinkled skin.

In a further embodiment, the invention is directed to methods for producing a product for use with mammals which includes eggshell membrane, physically processed eggshell membrane, eggshell membrane isolates and combinations thereof in a product for use with mammals. Preferably, the eggshell membrane is first separated from the egg white, egg yolk and eggshell prior to preparation of mechanically processed eggshell membrane and eggshell membrane isolates. Specific naturally occurring substances can also be purified prior to incorporation into the product for use with mammals.

Although the present invention has been described with reference to hen eggshell membrane, one skilled in the art can easily ascertain the use of eggshell membrane from other fowl including emu, ostrich, etc. Furthermore, in some examples the present application has been described with reference to a method for eggshell membrane enzyme hydrolysis and subsequent extraction and purification of naturally occurring eggshell membrane substances. One skilled in the art can easily ascertain various methods for eggshell membrane hydrolysis, and for extraction and purification of naturally occurring components (i.e., hyaluronic acid, glucosamine, chondroitin sulfate, growth factors) from eggshell membrane. Such equivalents are intended to be encompassed in the scope of the present invention.

EXAMPLES

The following non-limiting examples have been carried out to illustrate embodiments of the invention.

Example 1

Hen eggshells and attached eggshell membrane (ESM) were obtained from an egg breaking facility. The eggshell membrane was first separated from eggshells. Eggshell membrane was partially dehydrated, collected and immediately packaged in plastic bags and placed in storage. Samples of eggshell membrane were later retrieved for composition analyses. Results of these analyses are shown in Table 1.

TABLE 1

Typical Analysis of Dry Eggshell Membrane

| Component | % ESM |
| --- | --- |
| Water | 13.9 |
| Protein | 82.2 |
| Fat | 2.7 |
| Carbohydrate | 0.6 |
| Ash | 0.6 |

Example 2

The following example relates to the preparation of ESM flakes and powder. Hen eggshells and attached eggshell membrane were obtained from an egg breaking facility. The eggshell membrane was first separated from eggshells. Eggshell membrane flakes were collected and immediately packaged in plastic bags and placed in storage. Powdering was accomplished using standard milling or pulverizing procedures to treat eggshell membrane flakes containing about 10% moisture. The powder was subsequently sized by screening the pulverized powder through a series of calibrated screens to produce a particle size range from 100-500 microns.

Example 3

The following example relates to the preparation of eggshell membrane isolates. Samples of eggshell membrane were subjected to enzyme hydrolysis using a yeast enzyme complex. The insoluble residue was allowed to gravity settle and the resultant yellowish, clear solution collected. The hydrolysate was analyzed for uronic acid using the carbazole calorimetric assay. Hydrolysate was shown to contain between 0.1-0.3% HA. Since eggshell membrane samples were diluted approximately 1:10, HA content was between 1-3% HA. The insoluble residue was collected and analyzed for collagen, glucosamine and chondroitin concentrations. The residue was high in hydroxyproline indicating a high concentration of collagen. The clear supernatant was stored at refrigerated temperatures.

Example 4

The following example relates to the preparation and evaluation of capsules for nutraceutical/therapeutic treatments in humans. Eggshell membrane was separated from eggshell by a mechanical method. The separated eggshell membrane was partially dehydrated and powdered using a pulverization mill. The powder was sized to produce powder from approximately 100 microns to approximately 500 microns. This powder was heat treated and placed in size "0" gelatin capsules, containing about 500 mg of eggshell membrane powder. An individual experiencing chronic joint pain volunteered to take one capsule per day. After approximately 3 days, the individual reported a significant reduction in joint pain. The pain returned when the individual stopped taking the capsules.

Example 5

The following example relates to examination of the preparation using a novel, multi-analyte immunoassay profile of 60 acute phase reactants, cytokines, growth factors, and hormones using the Rules Based Medicine technology at Charles River Laboratories. Eggshell membrane isolates prepared as in Example 3, were filtered through 0.2 micron filters and mixed with eggshell membrane powder as prepared in Example 2. Sprague Dawley rats, aged 8-12 weeks, were given the composite powder (called NEM) prepared as a 10% w/v dispersion in 0.5% carboxymethylcellulose. The material was administered orally for 7 consecutive days. Blood samples were collected predose and at 24, 48, 72 hours, 14 and 28 days after the final dose via jugular vein. Blood samples were collected in potassium EDTA, spun down for undiluted plasma, frozen and shipped to CRL in Austin, Tex. for analysis.

Concentrations were below detectable levels for 20 of the 60 parameters. Of the measurable analytes, no treatment-related effects were recorded for II parameters; C reactive protein, Fibrinogen, IL-4, IL-10, Insulin, Leptin, Leukemia Inhibitory Factor, Macrophage-colony Stimulating Factor, Macrophage-derived Chemokine, Serum Glutamic-Oxaloacetic Transaminase, Vascular Cell Adhesion Molecule-1.

NEM treatment produced mild to moderate effects on 29 parameters. NEM decreased Apolipoprotein A1, Eotaxin, Fibroblast Growth Factor-9, Granulocyte Chemotactic Protein-2, Growth Hormone, Haptoglobulin, Immunoglobulin A, IL-1, IL-11, IL-12p70, IL-1$\alpha$, IL-2, IL-7, Lymphotactin, Inducible Protein-10, Monocyte Chemoattractant Protein-1, Monocyte Chemoattractant Protein-3, Monocyte Chemoattractant Protein-5, Macrophage Inflammatory Protein-1$\beta$ (MIP-1$\beta$), Myoglobin, Oncostatin M, Macrophage Inflammatory Protein-2 (MIP-2), Macrophage Inflammatory Protein 3-$\beta$, RANTES, Stem Cell Factor, Tissue Inhibitor of Metalloproteinase Type-1, Tumor Necrosis Factor-$\alpha$, and Vascular Endothelial Cell Growth Factor (VEGF). NEM increased von Willebrand factor.

Most obvious changes were noted for decreased levels of pro-inflammatory chemokines including IL-11, IL-1$\beta$, IL-2, IL-7, MIP-1$\beta$, MIP-2, and RANTES. Anti-inflammatory chemokines IL-4, IL-6, and IL-10 were not affected by NEM treatment. See Table 2.

TABLE 2

Reduction in Proinflammatory Cytokines following NEM Ingestion

| Antigen | Pretreatment | Day 7 | Day 21 | Day 35 |
|---|---|---|---|---|
| IL-11 (pg/ml) | 119.3 | 68.7 | 44.7 | 26.7 |
| IL-1alpha (pg/ml) | 190.7 | 23 | 13.6 | 10.8 |
| IL-2 (pg/ml) | 108.3 | 20 | 3 | 0 |
| IL-7 (ng/ml) | 0.287 | 0.057 | 0.033 | 0.008 |
| MCP-1 (pg/ml) | 720 | 439 | 250 | 236 |
| MCP-3 (pg/ml) | 354 | 226 | 135 | 116 |
| MCP-5 (pg/ml) | 6.93 | 2.07 | 0 | 0 |
| MIP-1beta (pg/ml) | 250 | 80 | 38 | 30 |
| MIP-2 (pg/ml) | 15.3 | 3.1 | 1.1 | 0 |
| MIP-3 beta (ng/ml) | 0.065 | 0.04 | 0.023 | 0.032 |
| RANTES (pg/ml) | 196 | 92 | 23 | 20 |
| TNF alpha (ng/ml) | 0.203 | 0.64 | 0.032 | 0.016 |
| VEGF (pg/ml) | 429 | 214 | 165 | 144 |

Statistically significant reductions in antigen levels were calculated for inflammatory antigens as shown in Table 3.

TABLE 3

Statistically Significant Reductions in Plasma Antigens following NEM Treatment in Rats

| Antigen | Day | Probability level |
|---|---|---|
| IL-11 | 35 | <0.05 |
| IL-1$\alpha$ | 7–35 | <0.05 |
| IL-2 | 7–35 | <0.005 |
| IL-7 | 35 | <0.005 |
| MCP-1 | 21–35 | <0.005 |
| MCP-3 | 21–35 | <0.005 |
| MCP-5 | 21–35 | <0.005 |
| MIP-1$\beta$ | 35 | <0.005 |
| MIP-2 | 7–35 | <0.005 |
| MIP-3$\beta$ | 21 | <0.05 |
| RANTES | 21–35 | <0.01 |
| TNF$\alpha$ | 35 | <0.005 |
| VEGF | 21–35 | <0.005 |

As shown in Table 3, many of the proinflammatory cytokines were significantly reduced in plasma following oral treatment with NEM, including TNF$\alpha$ and IL-1. These data support results from two open label clinical investigations and one randomized, blinded investigation (Example 6). All three investigations reported an overall reduction in joint pain. One open label study also showed significant increases in range of motion in subjects ingesting NEM. However, pain reduction in the randomized, blinded investigation was most evident in subjects exhibiting grade III osteoarthritis of the knee. More severe osteoarthritis frequently exhibits inflammatory activity that is almost indistinguishable from subjects with rheumatoid arthritis. The broad reduction in plasma proinflammatory cytokines reported in the present study correlates well with the noted effect of NEM in subjects with more severe (grade III) osteoarthritis.

Example 6

Eggshell membrane powder prepared as in Example 2 was mixed with hydrolyzed eggshell membrane isolates as prepared in Example 3 (in combination-NEM) and compared to placebo in a randomized, blinded, controlled clinical study in subjects exhibiting Class I to III osteoarthritis of the knee. Results showed that NEM treatment improved pain-related scores to a greater extent than placebo treatment. Differences in NEM and placebo were particularly significant in subjects exhibiting Class III osteoarthritis.

Processed eggshell membrane powder alone, or in combination with eggshell membrane hydrolysate, appears to be effective in reducing pain associated with joint inflammation and discomfort. The results from the rat plasma antigen study suggest that a reduction in pain may be associated with reduction in pro-inflammatory antigens following NEM consumption.

All references, including patents, publications, and patent applications, mentioned in this specification are herein incorporated by reference in the same extent as if each independent publication, patent or patent application was specifically and individually indicated to be incorporated by reference.

Thus, while there has been disclosed what is presently believed to be the preferred embodiments of the invention, those skilled in the art will appreciate that other and further changes and modifications can be made without departing from the scope or spirit of the invention, and it is intended that all such other changes and modifications are included in an are within the scope of the invention.

What is claimed is:

1. A method for reducing plasma pro-inflammatory cytokine levels in a mammal suffering from a condition selected from the group consisting of osteoarthritis, rheumatoid arthritis, rheumatism, bursitis, and degenerative spinal disc disease, the method comprising systemically administering an effective amount of a composition consisting essentially of naturally occurring egg shell membrane, and optionally, eggshell membrane isolates and/or hydrolysates to said mammal.

2. The method according to claim 1, wherein the osteoarthritis is grade III.

3. The method according to claim 1, wherein the proinflammatory cytokine is IL-1α.

4. The method according to claim 1, wherein the proinflammatory cytokine is IL-1β.

5. The method according to claim 1, wherein the proinflammatory cytokine is IL-2.

6. The method according to claim 1, wherein the proinflammatory cytokine is IL-7.

7. The method according to claim 1, wherein the proinflammatory cytokine is MCP-1.

8. The method according to claim 1, wherein the proinflammatory cytokine is MCP-3.

9. The method according to claim 1, wherein the proinflammatory cytokine is MCP-5.

10. The method according to claim 1, wherein the proinflammatory cytokine is MIP-1f3.

11. The method according to claim 1, wherein the proinflammatory cytokine is MIP-3f3.

12. The method according to claim 1, wherein the proinflammatory cytokine is RANTES.

13. The method according to claim 1, wherein the proinflammatory cytokine is TNF α.

14. The method according to claim 1, wherein the proinflammatory cytokine is VEGF.

15. A method for reducing plasma pro-inflammatory cytokine levels in a mammal suffering from a condition selected from the group consisting of osteoarthritis, rheumatoid arthritis, rheumatism, bursitis, and degenerative spinal disc disease, the method comprising systemically administering an effective amount of a composition consisting essentially of eggshell membrane isolates and/or hydrolysates to said mammal.

* * * * *